United States Patent [19]

Sonoda et al.

[11] Patent Number: 6,127,583

[45] Date of Patent: Oct. 3, 2000

[54] PROCESS FOR PREPARING ACETYLENE DERIVATIVE FROM A KETONE COMPOUND

[75] Inventors: Hiroshi Sonoda; Kazunari Okada; Kenichi Goto; Kouki Fukumura; Junko Naruse; Hidetoshi Hayashi; Teruyuki Nagata; Akira Takahashi, all of Fukuoka-ken, Japan

[73] Assignee: Mitsui Chemicals, Inc., Japan

[21] Appl. No.: 09/282,436

[22] Filed: Mar. 31, 1999

[30] Foreign Application Priority Data

| Apr. 7, 1998 | [JP] | Japan | ................................. | 10-094723 |
| Aug. 18, 1998 | [JP] | Japan | ................................. | 10-232050 |
| Aug. 19, 1998 | [JP] | Japan | ................................. | 10-233123 |

[51] Int. Cl.$^7$ ........................... C07C 15/48; C07C 15/54; C07C 39/18

[52] U.S. Cl. .......................... 568/716; 544/334; 546/186; 548/300.1; 548/320.5; 548/347.1; 568/939; 585/400; 585/534; 564/225; 564/509; 564/510

[58] Field of Search ......................... 548/300.1; 568/716, 568/939; 585/400, 534

[56] References Cited

U.S. PATENT DOCUMENTS 3,427,320 2/1969 Ogden .................................. 548/347.1

FOREIGN PATENT DOCUMENTS

| 59-25375 | 2/1984 | Japan | ................................. | 548/347.1 |
| 59-39851 | 3/1984 | Japan | ................................. | 548/347.1 |

*Primary Examiner*—Floyd D. Higel
*Attorney, Agent, or Firm*—Burns, Doane, Swecker, & Mathis, L.L.P.

[57] ABSTRACT

A preparation process of an acetylene derivative comprising reacting a compound having a skeleton represented by the formula (1):

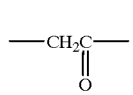

(1)

in the molecular formula with a compound represented by the formula (2):

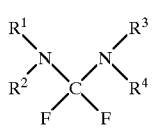

(2)

wherein $R^1$, $R^2$ $R^3$ and $R^4$ are individually an alkyl group having 1 to 6 carbon atoms and can be the same or different, $R^1$ and $R^3$ can bond each other to form a ring, and $R^1$ and $R^2$ or $R^3$ and $R^4$ can be bond each other to form one or two heterocyclic rings: or with a compound represented by the formula (3): wherein $R^1$, $R^2$, $R^3$ and $R^4$ are the same as in the formula (2), and $X_1$ is a

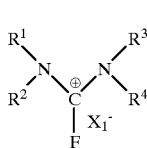

(3)

chlorine, bromine or iodine atom.

18 Claims, No Drawings

PROCESS FOR PREPARING ACETYLENE DERIVATIVE FROM A KETONE COMPOUND

BACKGROUND OF THE INVENTION

1. Field of the Invention

The present invention relates to a process for preparing an acetylene derivative, and more specifically to a process for preparing an acetylene compound by reacting a compound having two or more hydrogen atoms on the α-located carbon of a carbonyl group with a bis-disubstituted aminodifluoromethane compound or fluoroformamidinium=halogenide.

2. Related Art of the Invention

Acetylene compounds are extremely useful for the synthetic intermediate of agricultural chemicals and medicines and as a monomer which is convertible into a high strength polymer by crosslinking without variation of a molecular chain structure or development of moisture and other gases.

Thus, the demand has steadily increased. Particularly, it has been reported recently in Japanese Laid-Open Patent HEI 9-71651 and tried that polyimide resin and other polymers having excellent heat resistance, chemical resistance, electrical property and mechanical strength can further enhance these properties by terminating the polymer chain or branch of these polymers with the acetylene compounds or by using the acetylene compounds as an oligomer.

Acetylene derivatives can be commonly prepared by various processes disclosed in patents. For example, Soviet Patent 943234 and Japanese Laid Open Patent HEI 6-145078 have described a process for reacting an acetylene compound with other compounds. Similarly, Japanese Patent SHO 50-3299 and U.S. Pat. No. 3,303,229 have disclosed a process that a compound having a double bond is once halogenated and successively dehydrohalogenated to obtained the acetylene derivative. Further, U.S. Pat. No. 4,120,909 has taught a process for heating a compound having two or more hydrogen atoms on the α-located carbon to a carbonyl group at 600° C. in the presence of a vanadium catalyst.

The conventional preparation process of hydroxyphenylacetylene has been reported, for example, in Izv. Akad. Nauk SSSR Se. r. Khim 1964(11), 2073-4. In the process, 4-hydroxyacetophenone is chlorinated with phosphorus pentachloride, reacted in liquid ammonia in the presence of metallic sodium and ammonium chloride, and successively treated with water to obtain 4-hydroxyphenylacetylene in 46% yield.

Further, *Chem. Ber.* 99(9), 2822-7(1966) described a process for obtaining 3-hydroxyphenylacetylene in 21% yield by way of five step reactions from 3-benzoyloxybenzaldehyde.

In the process described in Bull. Chem. Soc. Japan 29, 470-1(1956), benzofuran is heat-refluxed in the presence of pyridine and metallic sodium and thereafter treated with water to obtain 2-hydroxyphenylacetylene in 54% yield.

In recent year, Polymer. Prepar. 1993, 34(1), 511-12. and Japanese Laid Open Patent HEI 8-217698 have described a process that 3- or 4-halophenol having a protected hydroxyl group, when necessary, is subjected to coupling with trimethylsilylacetylene or other monosilylacetylene in a triethylamine solvent in the presence of a palladium catalyst and thereafter subjected to removing of the silyl group and where necessary, deprotecting of the hydroxyl group to obtain desired hydroxyphenylacetylene in a considerably high yield of 60 to 80%.

Conventional processes above has low yield, require severe synthetic conditions, employ expensive materials and suffer from other problems in industry. Thus, further improvement has been desired.

SUMMARY OF THE INVENTION

As a result of an intensive investigation in order to solve these subjects, the present inventors have found that a compound represented by the formula (2)

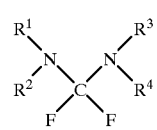

(2)

wherein $R^1$, $R^2$, $R^3$ and $R^4$ are individually an alkyl or aryl group having 1 to 6 carbon atoms and can be the same or different, $R^1$ and $R^3$ can bond to each other to form a ring, and $R^1$ and $R^2$ or $R^3$ and $R^4$ can bond to each other to form one or two heterocyclic rings: or with a compound represented by the formula (3):

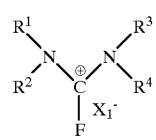

(3)

wherein $R^1$, $R^2$, $R^3$ and $R^4$ are the same as in the formula (2), and $X_1$ is a chlorine, bromine or iodine atom react with ketone having two α-located hydrogen atoms and convert the ketone group with ease into an acetylene group.

The inventors have further found that the compounds of the formula (2) and formula (3) can achieve economy because these compounds can be recovered after finishing the reaction and can be reused as halogenating agents. Thus the present invention has been completed.

That is, various aspects of the invention are illustrated in (a) to (g) below.

(a) A preparation process of an acetylene derivative comprising reacting a compound having a backbone represented by the formula (1):

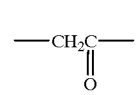

(1)

in the molecular formula with a compound represented by the formula (2):

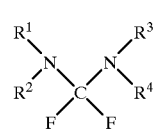

(2)

wherein $R^1$, $R^2$, $R^1$ and $R^4$ are individually an alkyl or aryl group having 1 to 6 carbon atoms and can be the same or different, $R^1$ and $R^3$ can bond to each other to form a ring, and $R^1$ and $R^2$ or $R^3$ and $R^4$ can bond to each other to form one or two heterocyclic rings: or with a compound represented by the formula (3):

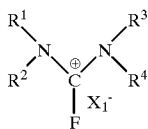

(3)

wherein $R^1$, $R^2$, $R^3$ and $R^4$ are the same as in the formula (2), and $X_1$ is a chlorine, bromine or iodine atom.

(b) A preparation process of an acetylene derivative according to the above (a) wherein the compound having the backbone of the formula (1) is a compound represented by the formula (4):

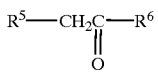

(4)

wherein $R^5$ and $R^6$ are individually a hydrogen atom, or a substituted or unsubstituted alkyl, substituted or unsubstituted aralkyl, substituted or unsubstituted aryl or substituted or unsubstituted heterocyclic group, can be the same or different, and the alkyl, aralkyl, aryl or heterocyclic group can include a hetero-atom and/or a substituent having a hetero-atom, except a compound having a carbonyl group bonded directly with the hetero-atom; and the acetylene derivative is an acetylene compound represented by the formula (5):

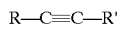

(5)

wherein R and R' are the same as in the formula (4).

(c) A preparation process of an acetylene derivative according to the above (b) wherein the compound represented by the formula (4) is acetophenone represented by the formula (6):

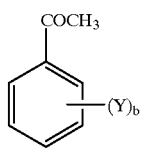

(6)

wherein b is an integer of 1 to 5, and Y can be the same or different and is individually a hydrogen atom, an alkyl, aryl, aralkyl, acetyl, hydroxyl, nitro, amino, amide, cyano, carboxylic acid, carboxylate ester, carboxylic anhydride or alkoxy group, or a halogen atom; and the acetylene derivative is phenylacetylene represented by the formula (7):

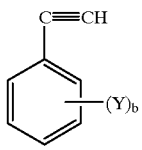

(7)

wherein Y and b are the same as in the formula (6).

(d) A preparation process of an acetylene derivative according to the above (c) wherein acetophenone represented by the formula (6) is hydroxyacetophenone represented by the formula (8):

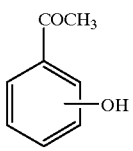

(8)

and the phenylacetylene derivative is hydroxyphenylacetylene represented by the formula (9):

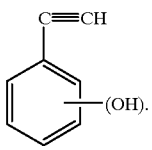

(9)

(e) A preparation process of an acetylene derivative according to the above (c) wherein acetophenone represented by the formula (6) is nitro-acetophenone represented by the formula (10):

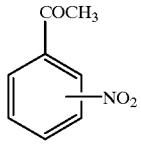

(10)

and the phenylacetylene derivative is nitro-phenylacetylene represented by the formula (11):

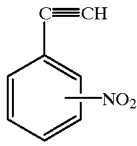

(11)

(f) A preparation process of an acetylene derivative according to the above (b) wherein the compound represented by the formula (4) is a compound represented by the formula (12):

(12)

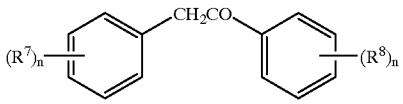

wherein n is an integer of 1 to 4 and $R^7$ and $R^8$ are the same or different and individually a substituted or unsubstituted alkyl, substituted or unsubstituted aralkyl, substituted or unsubstituted aryl group or a nitro, amino, amide, carboxylic acid, carboxylate ester, carboxylic anhydride, hydroxyl or cyano group, and the acetylene derivative is diphenylacetylene represented by the formula (13):

(13)

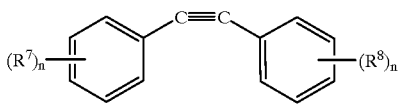

wherein n, $R^7$ and $R^8$ are the same as in the formula (12).

(g) A preparation process of an acetylene derivative according to one of the above (a) to (f) wherein the compound represented by the formula (2) is 2,2-difluoro-1,3-dimethylimidazolidine represented by the formula (14):

(14)

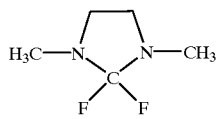

(h) A preparation process of an acetylene derivative according to one of the above (a) to (f) wherein the compound represented by the formula (3) is 2-fluoro-1,3-dimethylformamidinium=halogenide represented by the formula (15):

(15)

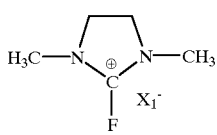

wherein $X_1$ is a chlorine, bromine or iodine atom.

The invention is a novel preparation process of acetylene compounds. Conventional preparation process of acetylene compounds required many steps and expensive raw materials and thus has been unsatisfactory to the preparation process in industry.

The invention can react a ketone compound having two α-hydrogen atoms with bis-disubstituted amino-difluoromethane or fluoroformamidinium=halide, and thus can prepare acetylene compounds in one step under mild reaction conditions. Consequently, the invention paves the road for an advantageous preparation process of the acetylene compounds in industry.

PREFERRED EMBODIMENTS OF THE INVENTION

The compounds represented by the formula (2) and formula (3) are used in the invention.

In these formulas, $R^1$, $R^2$, $R^3$ and $R^4$ are the same or different and represent a substituted or unsubstituted, saturated or unsaturated alkyl group or a substituted or unsubstituted aryl group, $R^1$ and $R^2$ or $R^3$ and $R^4$ can bond to each other to form a ring including or free from a hetero-atom.

Alternatively, $R^1$ and $R^3$ can bond to each other to form a ring including or free from a hetero-atom.

Preferred groups are an alkyl group having 1 to 6 carbon atoms and an aryl group. The alkyl group can be straight or branched.

That is, representative alkyl and aryl groups are a methyl, ethyl, n-propyl, allyl, isopropyl, n-butyl, butenyl, n-hexyl and phenyl group, and can be the same or different. $R^1$ and $R^2$ or $R^3$ and $R^4$ can bond to each other to form a nitrogen-heterocyclic group having 3 to 5 carbon atoms. Representative groups include, for example, a pyrrolidine group and piperidine group.

Further, $R^1$ and $R^3$ can bond to each other to form a five- or six-membered heterocyclic group having two nitrogen atoms.

Exemplary groups include an imidazolidine group, imidazolidinone group, pyrimidine group and pyrimidinone group.

Preferred specific compounds represented by the formula (2) include, for example, bis-dimethylamino-difluoromethane,
bis-diethylamino-difluoromethane,
bis-di-n-propylamino-difluoromethane,
bis-di-isopropylamino-difluoromethane,
bis-di-allylamino-difluoromethane,
bis-di-n-butylamino-difluoromethane,
bis-di-n-hexylamino-difluoromethane,
bis-(1-pyrrolidyl)-difluoromethane,
bis(1-piperidyl)-difluoromethane,
2,2-difluoro-1,3-dimethyl-imidazolidine,
2,2-difluoro-1,3-diethyl-imidazolidine,
2,2-difluoro-1,3-di-n-propyl-imidazolidine,
2,2-difluoro-1,3-diisopropyl-imidazolidine,
2,2-difluoro-1,3-diallyl-imidazolidine,
2,2-difluoro-1,3-di-n-butyl-imidazolidine,
bis(N-methyl-N-phenyl)difluoromthane,
2,2-difluoro-1,3-dimethyl-imidazolidine-4,5-dione,
2,2-difluoro-1,3-di-n-butyl-imidazolidine-4,5-dione, and
2,2-difluoro-1,3-dimethyl-pyrimidine.

Specific examples of the compounds represented by the formula (3)
include tetramethyl-2-fluoroformamidinium=chloride,
tetraethyl-2-fluoroformamidinium=chloride,
tetra-n-propyl-2-fluoroformamidinium=chloride,
tetraisopropyl-2-fluoroformamidinium=chloride,
tetra-n-butyl-2-fluoroformamidinium=chloride,
tetra-n-pentyl-2-fluoroformamidinium=chloride,
tetra-n-hexyl-2-fluoroformamidinium=chloride,
2-fluoro-1,3-dimethyl-imidazolinium=chloride,
2-fluoro-1,3-diethyl-imidazolinium=chloride,
2-fluoro-1,3-di-n-propyl-imidazolinium=chloride,
2-fluoro-1,3-di-n-butyl-imidazolinium=chloride,
2-fluoro-1,3-di-n-pentyl-imidazolinium=chloride,
2-fluoro-1,3-di-n-hexyl-imidazolinium=chloride,
N,N-dimethyl-N', N'-dimethylphenyl-fluoroformamidinium=chloride,
fluoro-bis(1-piperidyl)methylium=chloride,
tetramethyl-2-fluoroformamidinium=bromide,
tetraethyl-2-fluoroformamiddinium=bromide,
tetra-n-propyl-2-fluoroformamidinium=bromide,
tetraisopropyl-2-fluoroformamidinium=bromide, tetra-n-butyl-2-fluoroformamidinium=bromide,
tetra-n-pentyl-2-fluoroformamidinium=bromide,
tetra-n-hexyl-2-fluoroformamidinium=bromide,
2-fluoro-1,3-dimethyl-imidazolinium=bromide,
2-fluoro-1,3-diethyl-imidazolinium=bromide,
2-fluoro-1,3-di-n-propyl-imidazolinium=bromide,
2-fluoro-1,3-di-n-butyl-imidazolinium=bromide,
2-fluoro-1,3-di-n-pentyl-imidazolinium=bromide,
2-fluoro-1,3-di-n-hexyl-imidazolinium=bromide,
N,N-dimethyl-N',N'-dimethylphenyl-fluoroformamidinium=bromide,
fluoro-bis(1-piperidyl)methylium=bromide,
tetramethyl-2-chloroformamidinium=bromide,
tetraethyl-2-chloroformamidinium=bromide,
2-chloro-1,3-dimethyl-imidazolinium=bromide,
2-chloro-1,3-diethyl-imidazolinium=bromide,
tetramethyl-2-fluoroformamidinium=iodide,
tetraethyl-2-fluoroformamidinium=iodide,
tetra-n-propyl-2-fluoroformamidinium=iodide,
tetraisopropyl-2-fluoroformamidinium=iodide,
tetra-n-butyl-2-fluoroformamidinium=iodide,
tetra-n-pentyl-2-fluoroformamidinium=iodide,
tetra-n-hexyl-2-fluoroformamidinium=iodide,
2-fluoro-1,3-dimethyl-imidazolinium=iodide,
2-fluoro-1,3-diethyl-imidazolinium=iodide,
2-fluoro-1,3-di-n-propyl-imidazolinium=iodide,
2-fluoro-1,3-di-n-butyl-imidazolinium=iodide,
2-fluoro-1,3-di-n-pentyl-imidazolinium=iodide,
2-fluoro-1,3-di-n-hexyl-imidazolinium=iodide,
N,N-dimethyl-N',N'-dimethylphenyl-fluoroformamidinium=iodide,
fluoro-bis(1-piperidyl)methylium=iodide,
tetramethyl-chloroformamidinium=iodide,
tetraethyl-2-chloroformamidinium=iodide,
2-chloro-1,3-dimethyl-imidazolinium=iodide,
2-chloro-1,3-diethyl-imidazolinium=iodide,
tetramethyl-2-iodoformamidinium=iodide,
tetraethyl-2-iodoformamidinium=iodide,
2-iodo-1,3-dimethyl-imidazolinium=iodide,
2-iodo-1,3-diethyl-imidazolinium=iodide.

These compounds are prepared in safety and with ease by carrying out a halogen exchange reaction of chloroformamidinium=chloride represented by the formula (16):

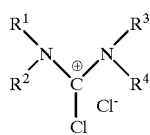

(16)

wherein $R^1$, $R^2$, $R^3$ and $R^4$ are the same as above, with an alkali metal salt of a desired atom in an inert solvent such as acetonitrile and 1,3-dimethyl-2-imidazolidinone. Of course, it presents quite no problem to use a bromine atom in place of the chlorine atom in the formula (16).

Specific alkali metal salts which can be used for the preparation of the compound represented by the formula (2) include, for example, cesium fluoride, rubidium fluoride, potassium fluoride and sodium fluoride. Spray dried potassium fluoride for use in a fluorination reaction is preferred in view of economy and reaction efficiency. The compound of the formula (3) can also be prepared by using a corresponding alkali metal salt.

Chloroformamidinium=chloride represented by the formula (16) is used as a raw material for preparing the compound represented by the formulas (2) and (3). The chloride of the formula (16) can be prepared by chlorination of tetraalkylurea, tetraalkylthiourea, 1,3-dialkylimidazolidinone or 1,3-dialkylimidazolidine-2-thione with a chlorinating agent such as phosgene and thionyl chloride.

For example, 2-chloro-1,3-dimethylimidazolinium=chloride can be prepared with ease by the process described in Japanese Laid Open Patent SHO 59-25375.

When a difluoro compound is used in the preparation of a compound represented by the formula (2), the amount of alkali metal fluoride is usually 2 mole or more, preferably 2 to 5 mols for one mol of the compound represented by the formula (16). When the amount of alkali metal chloride is less than 2 moles, the reaction is in sufficient and unreacted chloride remains. On the other hand, use of more than 5 moles does not so much increase the yield.

In the preparation of a compound having a chlorine counter ion, the amount of alkali metal fluoride for use in the halogen exchange reaction is usually one mol or more, preferably 1 to 1.1 moles for one mol of the compound represented by the formula (6).

When the amount is less than one mol, the reaction is insufficient and unreacted chloride remains. On the other hand, use of more than 1.1 mols tends to increase formation of a difluoro compound. In order to prepare a compound having bromine or iodine counter ion, one of the chlorine atom is replaced by a fluorine atom in the first step, and thereafter a halogen exchange reaction can be carried out by using one equivalent of alkali metal bromide or alkali metal iodide. Alternatively, two chlorine atoms are replaced by two fluorine atoms in the first step and successively the desired compound can be obtained by reacting with one equivalent of alkali metal bromide or alkali metal iodide.

No particular restriction is imposed upon the reaction solvent of the halogen exchange reaction so long as the solvent does not react with chloroformamidinium=chloride and the product compound represented by the formula (2) or the formula (3). Preferred solvents are acetonitrile, dimethylformamide, 1,3-dimethyl-2-imidazolidinone, dichloromethane and ethylene dichloride.

No particular limitation is imposed upon the amount of the solvent. The preferred amount is usually 1 to 10 times by weight of reactive substance in view of reaction efficiency and operation control.

The temperature of halogen exchange reaction is not limited in particular and is usually in the range of −20 to 150° C., preferably 0 to 100° C. in view of reaction velocity and stability of product.

The halogen exchange reaction of the compound represented by the formula (16) can also be carried out in the presence of a phase transfer catalyst including quaternary alkyl ammonium salt or quaternary alkyl phosphonium salt. The resulting compounds represented by the formula (2) and (3) can be used for the next reaction in the form of the halogen exchange reaction mass as such, or can be used for the next reaction after filtering off the inorganic salts, or can also be used after filtering off the inorganic salts and isolating from the resultant filtrate.

Some of the compounds of the formula (2) can be fractionated by distillation.

No particular restriction is imposed upon the ketone compound of the formula (1) having two or more hydrogen atoms on the α-located carbon of a carbonyl group so long as the compound has structure of the formula (1)

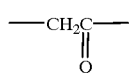

(1)

Preferred ketone compound is represented by the formula (4):

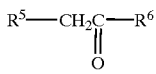

(4)

wherein $R^5$ and $R^6$ are a hydrogen atom, a substituted or unsubstituted alkyl, substituted or unsubstituted aralkyl, substituted or unsubstituted aryl, or substituted or unsubstituted heterocyclic group, and can be the same or different. The alkyl, aralkyl, aryl and heterocyclic group can include a hetero atom and/or a substituent having a hetero-atom, except a compound having a carbonyl group bonded with an oxygen atom or nitrogen atom.

Specific substituents represented by $R^5$ and $R^6$ include, for example, a hydrogen atom, a methyl, ethyl, n-propyl, isopropyl, n-butyl, i-butyl, t-butyl, n-pentyl, n-hexyl group, cyclohexyl, n-heptyl, n-octyl, and other substituted or unsubstituted alkyl group; a benzyl group, 2-phenylethyl, 3-phenylpropyl, 2-phenylpropyl, diphenylmethyl, methyl substituted benzyl, methoxy substituted benzyl, nitro substituted benzyl, haloganated benzyl, amino substituted benzyl, phenoxy benzyl, benzoyl benzyl and other substituted or unsubstituted aralkyl group; a phenyl, hydroxy substituted phenyl, nitro substituted phenyl, cyano substituted phenyl, carboxylic acid substituted phenyl, carboxylic anhydride substituted phenyl, carboxylic ester substituted phenyl, halogen substituted phenyl, acetyl substituted phenyl, naphthyl, methylphenyl, dimethylphenyl, methoxyphenyl, ethoxyphenyl, dimethoxyphenyl and other substituted or unsubstituted aryl group.

Fundamentally, no particular restriction is imposed upon the substituent so long as the substituent does not interfere with the reaction for forming the acetylene group. An evident interference takes place when the carbonyl group having the structure represented by the formula (4) makes a direct bond with an oxygen atom to form an ester compound, or bonds directly with a nitrogen atom to form an amide compound.

Preferred compounds represented by the formula (4) include, for example, alkyl ketone wherein $R^5$ and $R^6$ are individually the same or different alkyl group having 1 to 10 carbon atoms, hydroxyacetophenone wherein $R^5$ is a hydrogen atom and $R^6$ is a hydroxy substituted phenyl group, nitroacetophenone wherein $R^5$ is hydrogen atom and $R^6$ is a nitro substituted phenyl group, cyanoacetophenone wherein $R^5$ is a hydrogen and $R^6$ is a cyano substituted phenyl group, diacetylbenzene wherein $R^5$ is hydrogen atom and $R^6$ is an acetyl substituted phenyl group, diacetylbiphenyl wherein $R^5$ is a hydrogen atom and $R^6$ is an acetyl substituted biphenyl group, carbonyl chloride substituted acetophenone wherein $R^5$ is a hydrogen atom and $R^6$ is a carbonyl chloride substituted phenyl group, benzoyl substituted acetophenone wherein $R^5$ is a hydrogen atom and $R^6$ is a benzoyl substituted phenyl group, carboxylic anhydride substituted acetophenone wherein $R^5$ is a hydrogen atom and $R^6$ is a carboxylic anhydride substituted phenyl group, benzyl-dicarboxyphenyl ketone anhydride wherein $R^5$ is phenyl group and $R^6$ is a carboxylic anhydride substituted phenyl group, dibenzoic acid benzyl phenyl ketone anhydride wherein $R^5$ is a carboxylic anhydride substituted benzyl group and $R^6$ is phenyl group, and benzyl-nitrophenyl ketone wherein $R^5$ is a phenyl group and $R^6$ is a nitro substituted phenyl group. However, the invention is not limited by these exemplified compounds.

More preferred compounds are acetophenone represented by the formula

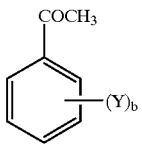

(6)

wherein b is an integer of 1 to 5, and Y is the same or different and individually a hydrogen atom, an alkyl, aryl, aralkyl, acetyl, hydroxyl, nitro, amino, amide, cyano, carboxylic acid, carboxylate ester, carboxylic anhydride, alkoxy group and a halogen atom.

Most preferred compounds are hydroxyacetophenone represented by the formula(8):

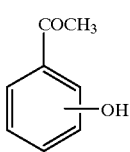

(8)

and nitro substituted acetophenone represented by the formula (10)

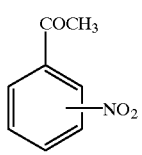

(10)

Further preferred compounds are acetophenone derivatives represented by the formula (12)

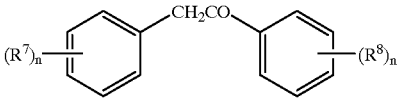

(12)

wherein n is an integer of 1 to 4, and $R^7$ and $R^8$ are the same or different, and are a substituted or unsubstituted alkyl, substituted or unsubstituted aralkyl, substituted or unsubstituted aryl, nitro, amino, amide, carboxylic acid, carboxylate ester, carboxylic anhydride, hydroxyl and cyano group.

These acetophenone compounds provide corresponding acetylene derivatives, respectively.

That is, phenylacetylene compounds represented by the formula (7):

(7)

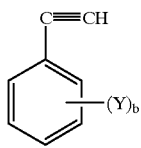

wherein b and Y are the same as in the formula (6), hydroxyphenylacetylene of the formula (9):

(9)

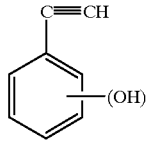

nitrophenylacetylene of the formula (11):

(11)

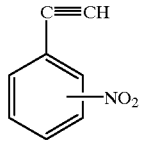

and more over, diphenylacetylene compounds represented by the formula (13):

(13)

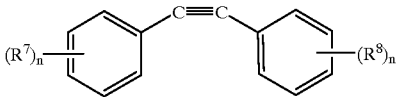

wherein n, $R^7$ and $R^8$ are the same as in the formula (12), can be obtained.

When the compound represented by the formula (2) or formula (3) is used for conversion of the compound represented by the formula (1) or formula (4) into an acetylene derivative, the amount of the compound represented by the formula (2) or formula (3) is 1 equivalent or more for the ketone group. However, in consideration of reaction efficiency, the amount of 1 to 10 equivalents is desired. The amount less than 1 equivalent is insufficient and remains an unreacted ketone group.

When the compound represented by the formula (4) or formula (6) has two or more backbones of the formula (1) in a same molecule, a compound having two or more acetylene groups can be prepared by reacting the multiple backbones compound with a stoichiometric amount of the compound represented by the formula (2) or formula (3).

When a compound having the backbone of the formula (1) or the formula (4) contains a carboxylic acid group or a carboxylic anhydride group, the carboxylic acid group is converted to a carboxylic acid halide group and the carboxylic anhydride group is converted to a dicarboxylic acid halide group.

The compound represented by the formula (2) or formula (3) performs an equimolar reaction respectively with a carboxylic acid group or carboxylic anhydride group to form a carboxylic acid halide or dicarboxylic acid halide. The reaction velocity is liable to be faster than that of the ketone group and thus the compound represented by the formula (2) or formula (3) is required in excess.

When a compound having the skeleton of the formula (1) or the formula (4) contains a hydroxyl substituted phenyl group, the hydroxyl group is liable to bond with the compound represented by the formula (2) or formula (3). Consequently, the compound represented by the formula (2) or formula (3) are required in excess. Additionally, the compound resulting from the bonding of a hydroxyl group with the compound of the formula (2) or formula (3) can be hydrolyzed with ease into a hydroxyl substituted acetylene compound and urea.

No particular restriction is imposed upon the solvent used for the above reaction so long as the solvent does not react with the compound represented by the formula (1) and formula (4) and the resulting acetylene derivative. Preferred solvents include acetonitrile, dichloromethane, chloroform, ethylene dichloride, glyme, diglyme, N-methylpyrrolidinone, dimethylformamide and 1,3-dimethyl-2-imidazolidinone.

Further, hydrogen halide capturing agents, bases, acids and catalysts can be added to the reaction so long as these matters do not give an adverse effect on the compound represented by the formula (2) or formula (3), the compound represented by the formula (1) and formula (4), and the reaction for preparing the acetylene derivative.

The reaction temperature is in the range of 0 to 150° C., preferably 20 to 120° C. At lower than 0° C., the reaction velocity is extremely slow and practically, no progress of the reaction can be observed. On the other hand, the temperature exceeding 150° C. is unfavorable because the compound represented by the formula (2) or formula (3) lowers stability.

The acetylene compound formed by the reaction can be isolated from the reaction mass by distillation or by pouring into water and successive separating procedure. When an unreacted compound of the formula (2) or formula (3) remains in the reaction mass, hydrogen halide generates in the step of pouring into water. Thus developed hydrogen halide can be captured by addition of sodium hydrogen carbonate. Further, the compound represented by the formula (2) or formula (3) can be recovered after finishing the reaction in the form of urea.

EXAMPLE

The present invention will hereinafter be illustrated by way of examples. However, these examples are not construed to limit the scope of the invention. In the acetonitrile solution of Synthesis Example 1, the concentration of 2,2-difluoro-1,3-dimethylimidazolidine (hereinafter referred to simply as DFI), 2-fluoro-1,3-dimethylimidazolinium=chloride (hereinafter referred to simply as DMFC), and 2-fluoro-1,3-dimethylimidazolidinium=bromide (hereinafter referred to simply as DMFB) was measured with high performance liquid chromatography (hereinafter referred to simply as HPLC) using the derivative obtained by individually reacting a certain amount of these compounds with aniline. The concentration of fluorine ion was determined by absorptiometry using a lanthanium-alizarin complexon reagent. Other halogen atoms are determined by the silver nitrate titrating method. The scanning range of GC-MS was M/Z≧50.

Synthesis Example 1

Synthesis of 2,2-difluoro-1,3-dimethylimidazolidine (DFI)

To a 500 ml four necked flask, 80.0 g (0.452 mol) of 2-chloro-1,3-dimethylimidazolinium=chloride, 105.1 g (1.810 mol) of spray dried potassium fluoride, and 320 ml of acetonitrile were charged and reacted at 80° C. for 17 hours under nitrogen atmosphere. After cooling the reaction mass to 25° C., inorganic salt was filtered off to obtain 414.2 g of an acetonitrile solution of DFI (MW 136.14). The solution had a DFI concentration of 11.4 wt %. The yield was 77%.

The solution was distilled under reduced pressure to obtain 32 g of DFI. The purity was 97.8%.

The product had following properties.

Boiling point: 47.0° C./37 mmHg, EIMS: 136 ($M^+$), 117$(M-F)^+$, IR (neat) $cm^{-1}$: 1486, 1385, 1295, 1242, 1085, 966, F-analysis: Calculated 27.9%, Found 27.7%, $^1$H-NM R (δ, ppm, $CDCl_3$ solvent, TMS reference): 2.52 (s, 6H, —$CH_3$×2), 3.05 (s, 4H, —$CH_2$—$CH_2$—), $^{13}$C-NMR (δ, ppm, $CDCl_3$ solvent, −45° C., $CDCl_3$ reference): 31.4 (s, —$CH_3$×2), 47.6 (s, —$CH_2$—$CH_2$—), 128.5 (t, J=230 Hz, =$CF_2$), $^{19}$F-NMR (δ, ppm, $CDCl_3$ solvent, −45° C., $CFCl_3$reference): −70.9 (s, =$CF_2$).

Synthesis Example 2

Synthesis of 1,3-dimethyl-2-fluoro-imidazolinium=chloride (DMFC)

To a 1 liter four necked flask, 118.4 g (0.70 mol) of 2-chloro-1,3-dimethylimidazolinium=chloride, 58.8 g (1.40 mol) of sodium fluoride and 408.5 g of acetonitrile were charged and reacted at 84° C. for 8 hours under nitrogen atmosphere. After cooling the reaction mass to 25° C., inorganic salt was filtered off to obtain an acetonitrile solution of DMFC (MW 152.60). DMFC had a concentration of 19.3 wt % by a guanidine method. The acetonitrile solution had following physical properties.

FABMS: 117[$(DMFC-Cl)^+$], 269[$(2×DMFC-Cl)^+$], F-analysis: Calculated 2.57 wt %, Found 2.56 wt %, Cl-analysis: Calculated 4.79 wt %. Found 4.87 wt %, $^1$H-NMR (δ, ppm, $CH_3CN$ solvent, $CH_3CN$ reference, 25° C.): 2.98 (s, 6H, —$CH_3$×2), 3.91 (s, 4H, —$CH_2$—$CH_2$—), $^{13}$C-NMR (δ, ppm, $CH_3CN$ solvent, DMSO-$d_6$ reference 25° C.): 31.3 (s, —$CH_3$), 46.8 (s, —$CH_2$—), 157.7 (d, J=280Hz, C-F).

Example 1

Synthesis of phenylacetylene

To a reaction vessel, 1.06 g (8.82 mmol) of acetophenone, 2.43 g (17.85 mmol) of DFI and 25 ml of acetonitrile were charged and reacted at 84° C. for 10 hours under nitrogen atmosphere. After finishing the reaction, GC-MS measurement of the reaction mixture was carried out. As a result, formation of phenylacetylene was confirmed (parent ion 102, base peak 102). The yield of the reaction was 30% by GC-analysis.

Example 2

Synthesis of phenylacetylene

To a reaction vessel, 1.06 g (8.82 mmol) of acetophenone, and 7.85 g of a 16.5 wt % DMFC/acetonitrile solution [1.48 g (9.73 mmol) as DMFC] were charged and reacted at 84° C. for 22 hours under nitrogen atmosphere. After finishing the reaction, formation of phenylacetylene (parent ion 102, base peak 102) by GC-MS analysis of the reaction mixture. The yield of the reaction was 12% by GC-analysis.

Example 3

Synthesis of diphenylacetylene

To a reaction vessel, 1.96 g (9.99 mmol) of benzylphenylketone, 2.75 g (27.24 mmol) of DFI and 25 ml of acetonitrile were charged and reacted at 84° C. for 32 hours under nitrogen atmosphere. After finishing the reaction, formation of diphenylacetylene (parent ion 178, base peak 188) was confirmed by GC-MS analysis of the reaction mixture. The yield of the reaction was 50%.

Example 4

Synthesis of 2-octyne and 3-octyne

To a reaction vessel, 1.03 g (8.03 mmol) of ethyl n-pentyl ketone, 2.21 g (16.20 mmol) of DFI, and 25 ml of acetonitrile were charged and reacted at 84° C. for 20 hours under nitrogen atmosphere. After finishing the reaction, formation of 2-octyne (parent ion 110, base peak 81) and 3-octyne (parent ion 110, base peak 67) were confirmed by GC-MS analysis of the reaction mixture. The conversion ratio of the reaction was 83%. The GC area ratio of 2-octyne and 3-octyne was 60:40.

Example 5

Synthesis of 3-nitrophenylacetylene

To a reaction vessel, 1.32 g (8.0 mmol) of 3-nitroacetophenone and 5 ml of a DMFC/acetonitrile solution [1.22 g (8.0 mmol) as DMFC] were charged and reacted at 84° C. for 4 hours under nitrogen atmosphere. After finishing the reaction, formation of 3-nitrophenylacetylene (parent ion 147, base peak 101) was confirmed by GC-MS analysis of the reaction mixture. As a result of GC analysis, the reaction yield of was 21% and the reaction selectivity was 94%.

Example 6

Synthesis of 3-nitrophenylacetylene

To a reaction vessel, 0.481 g (2.909 mmol) of 3-nitroacetophenone and 10 ml (10.826 mmol) of a DFI/acetonitrile solution 0.46 g (5.818 mmol) of pyridine were charged and reacted at 84° C. for 5 hours under nitrogen atmosphere. After finishing the reaction, formation of 3-nitrophenylacetylene (parent ion 147, base peak 101) was confirmed by GC-MS analysis of the reaction mixture. 3-Nitrophenylacetylene had the reaction yield of 36.4% and the reaction selectivity was 100%.

Example 7

Synthesis of diphenylacetylene

To a reaction vessel, 1.568 g (8.0 mmol) of benzyl phenyl ketone, 5 ml (8.0 mmol) of a DMFC/acetonitrile solution 5 ml of acetonitrile were charged and reacted at 84° C. for 5 hours under nitrogen atmosphere. After finishing the reaction, formation of diphenylacetylene (parent ion 178, base peak 188) was confirmed by GC-MS analysis of the reaction mixture. Diphenylacetylene had the reaction yield of 53% and the reaction selectivity was 84%.

Synthesis Example 3

Synthesis of 1,3-dimethyl-2-fluoro-imidazolinium=bromide (DMFB)

To a 50 ml reaction flask, 5.45 g (40.0 mmol) of 2,2-difluoro-1,3-dimethylimidazolidine, 4.12 g (40.0 mmol) of sodium bromide and 35.3 g of acetonitrile were charged and reacted at 20° C. for 14 hours under nitrogen atmosphere.

The acetonitrile solution layer of the reaction mixture was subjected to guanidine measurement and bromine analysis.

DMFB had a concentration of 17.67% (36.5 mmol) by the guanidine method. As a result of the bromine analysis, bromine had a concentration of 4.55% (24.1 mmol) in the reaction mixture. Consequently, DMFB in the reaction mixture was 24.1 mmol and unreacted DFI was 12.4 mmol.

Example 8

Synthesis of diphenylacetylene

To a reaction vessel, 1.520 g (7.745 mmol) of benzyl phenyl ketone, and 10 ml of the reaction mixture obtained in Synthesis Example 3 (corresponding to 6.025 mmol of DMFB and 3.10 mmol of DFI) were charged and reacted at 84° C. for 6 hours under nitrogen atmosphere. After finishing the reaction, formation of diphenylacetylene (parent ion 178, base peak 188) was confirmed by GC-MS analysis of the reaction mixture. Diphenylacetylene had the reaction yield of 69% and the reaction selectivity was 98% by GC analysis.

Example 9

Synthesis of 4-hydroxyphenylacetylene

To a 30 ml two necked flask equipped with a reflux condenser and magnetic stirrer, 1.23 g (9.03 mmol) of 4-hydroxyacetophenone and 10.76 g of a DFI/acetonitrile solution (corresponding to 9.62 mmol of DFI) were charged and reacted with heat refluxing for 5 hours under nitrogen atmosphere. As a result of GC analysis of the reaction mixture, the raw material 4-hydroxyacetophenone had a conversion ratio of 35.5% and the product 4-hydroxyphenylacetylene had the yield of 34.7% and selectivity of 97.7%.

Example 10

Synthesis of 4-hydroxyphenylacetylene

The same procedures as Example 9 were carried out except that 20.82 g of a DFI/acetonitrile solution (corresponding to 18.61 mmol of DFI) was used. As a result of GC analysis of the reaction mixture, the raw material 4-hydroxyacetophenone had a conversion ratio of 95.2% and the product 4-hydroxyphenylacetylene had the yield of 92.8% and selectivity of 97.5%.

What is claimed is:

1. A preparation process of an acetylene compound from a ketone compound comprising reacting a ketone compound having a backbone represented by the formula (1)

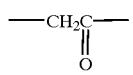
(1)

in the molecular formula with a compound represented by the formula (2)

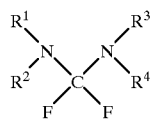
(2)

wherein $R^1$, $R^2$, $R^3$ and $R^4$ are individually an alkyl group having 1 to 6 carbon atoms and are the same or different, $R^1$ and $R^2$ are individual groups or are bonded to each other to form a ring, and $R^1$ and $R^2$ or $R^3$ and $R^4$ are individual groups or are bonded to each other respectively to form one or two heterocyclic rings: or with a compound represented by the formula (3)

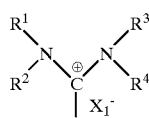
(3)

wherein $R^1$, $R^2$, $R^3$ and $R^4$ are the same as in the formula (2), and $X_1$ is a chlorine, bromine or iodine atom.

2. A preparation process of an acetylene compound according to claim 1 wherein the ketone compound having the backbone of the formula (1) is a compound represented by the formula (4):

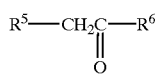
(4)

wherein $R^5$ and $R^6$ are individually a hydrogen atom, or a substituted or unsubstituted alkyl, substituted or unsubstituted aralkyl, substituted or unsubstituted aryl or substituted or unsubstituted heterocyclic group, and are the same or different, land or an alkyl, aralkyl, aryl or heterocyclic group including a hetero-atom and/or a substituent having a hetero-atom, except a compound having a carbonyl group bonded directly with the hetero-atom; and the acetylene compound is an acetylene compound represented by the formula (5):

(5)

wherein R and $R^1$ are the same as $R^5$ and $R^6$ in the formula (4).

3. A preparation process of an acetylene compound according to claim 2 wherein the compound represented by the formula (4) is acetophenone represented by the formula (6):

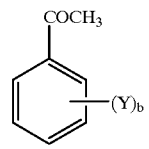
(6)

wherein b is an integer of 1 to 5, and Y is the same or different and is individually a hydrogen atom, an alkyl, aryl, aralkyl, acetyl, hydroxyl, nitro, amino, amide, cyano, carboxylic acid, or alkoxy group, or a halogen atom; and the acetylene compound is phenylacetylene represented by the formula (7):

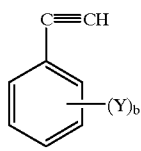

(7)

wherein Y and b are the same as in the formula (6).

4. A preparation process of an acetylene compound according to claim 3 wherein acetophenone represented by the formula (6) is hydroxyacetophenone represented by the formula (8):

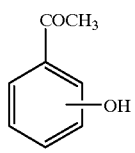

(8)

and the phenylacetylene derivative is hydroxyphenylacetylene represented by the formula (9):

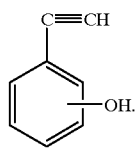

(9)

5. A preparation process an acetylene compound according to claim 3 wherein acetophenone represented by the formula (6) is nitro-substituted acetophenone represented by the formula (10):

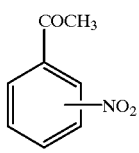

(10)

and the phenylacetylene is a nitro-substituted phenylacetylene compound represented by the formula (11):

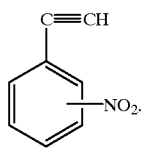

(11)

6. A preparation process of an acetylene compound according to claim 2 wherein the compound represented by the formula (4) is a compound represented by the formula (12):

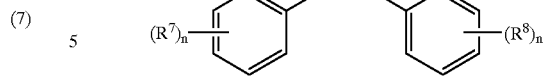

(12)

wherein n is an integer of 1 to 4 and $R^7$ and $R^8$ are the same or different and are individually a substituted or unsubstituted alkyl, substituted or unsubstituted aralkyl, substituted or unsubstituted aryl, nitro, amino, amide, carboxylic acid, hydroxyl or cyano group, and the acetylene compound is diphenylacetylene represented by the formula (13):

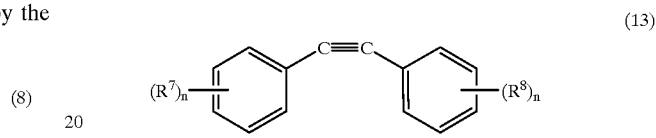

(13)

wherein n, $R^7$ and $R^8$ are the same as in the formula (12).

7. A preparation process of an acetylene compound according to claim 6 wherein the compound represented by the formula (2) is 2,2-difluoro-1,3-dimethylimidazoline represented by the formula (14):

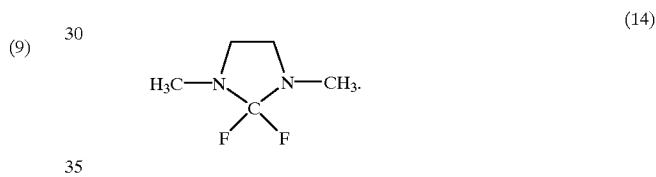

(14)

8. A preparation process of an acetylene compound according to claim 6 wherein the compound represented by the formula (3) is 2-fluoro-1,3-dimethylformamidinium=halogenide represented by the formula (15):

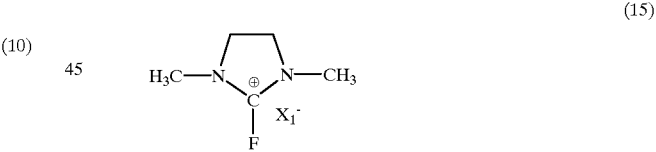

(15)

wherein $X_1$ is a chlorine, bromine or iodine atom.

9. A preparation process of an acetylene compound according to claim 5 wherein the compound represented by the formula (2) is 2,2-difluoro-1,3-dimethylimidazoline represented by the formula (14):

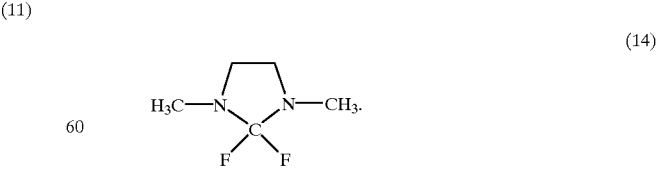

(14)

10. A preparation process of an acetylene compound according to claim 4 wherein the compound represented by the formula (2) is 2,2-difluoro-1,3-dimethylimidazoline represented by the formula (14):

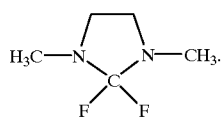
(14)

11. A preparation process of an acetylene compound according to claim 3 wherein the compound represented by the formula (2) is 2,2-difluoro-1,3-dimethylimidazoline represented by the formula (14):

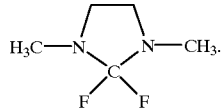
(14)

12. A preparation process of an acetylene compound according to claim 2 wherein the compound represented by the formula (2) is 2,2-difluoro-1,3-dimethylimidazoline represented by the formula (14):

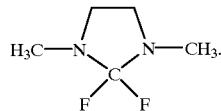
(14)

13. A preparation process of an acetylene compound according to claim 1 wherein the compound represented by the formula (2) is 2,2-difluoro-1,3-dimethylimidazoline represented by the formula (14):

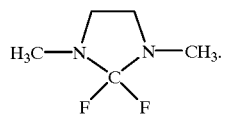
(14)

14. A preparation process of an acetylene compound according to claim 5 wherein the compound represented by the formula (3) is 2-fluoro-1,3-dimethylformamidinium=halogenide represented by the formula (15):

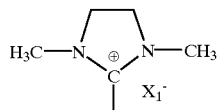
(15)

wherein $X_1$ is a chlorine, bromine or iodine atom.

15. A preparation process of an acetylene compound according to claim 4 wherein the compound represented by the formula (3) is 2-fluoro-1,3-dimethylformamidinium=halogenide represented by the formula (15):

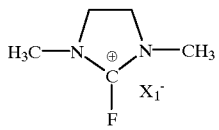
(15)

wherein $X_1$ is a chlorine, bromine or iodine atom.

16. A preparation process of an acetylene compound according to claim 3 wherein the compound represented by the formula (3) is 2-fluoro-1,3-dimethylformamidinium=halogenide represented by the formula (15):

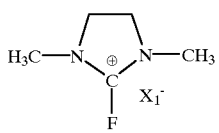
(15)

wherein $X_1$ is a chlorine, bromine or iodine atom.

17. A preparation process of an acetylene compound according to claim 2 wherein the compound represented by the formula (3) is 2-fluoro-1,3-dimethylformamidinium=halogenide represented by the formula (15):

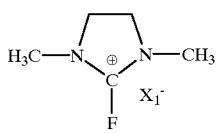
(15)

wherein $X_1$ is a chlorine, bromine or iodine atom.

18. A preparation process of an acetylene compound according to claim 1 wherein the compound represented by the formula (3) is 2-fluoro-1,3-dimethylformamidinium=halogenide represented by the formula (15):

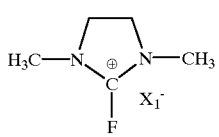
(15)

wherein $X_1$ is a chlorine, bromine or iodine atom.

* * * * *

UNITED STATES PATENT AND TRADEMARK OFFICE
CERTIFICATE OF CORRECTION

PATENT NO. : 6,127,583
DATED : October 3, 2000
INVENTOR(S) : Hiroshi Sonoda et al.

It is certified that error appears in the above-identified patent and that said Letters Patent is hereby corrected as shown below:

Column 16,
Line 40, delete "land".